(12) United States Patent
Nakagami et al.

(10) Patent No.: US 10,080,621 B2
(45) Date of Patent: Sep. 25, 2018

(54) SYRINGE NEEDLE DISPOSAL CONTAINER

(71) Applicant: FINE PRO CORPORATION, Koka-shi, Shiga (JP)

(72) Inventors: Hiroyuki Nakagami, Osaka (JP); Takumi Moro, Koka (JP)

(73) Assignee: FINE PRO CORPORATION, Koka (JP)

( * ) Notice: Subject to any disclaimer, the term of this patent is extended or adjusted under 35 U.S.C. 154(b) by 0 days.

(21) Appl. No.: 15/328,421

(22) PCT Filed: Jul. 28, 2015

(86) PCT No.: PCT/JP2015/071308
§ 371 (c)(1),
(2) Date: Jan. 23, 2017

(87) PCT Pub. No.: WO2016/017609
PCT Pub. Date: Feb. 4, 2016

(65) Prior Publication Data
US 2017/0209230 A1 Jul. 27, 2017

(30) Foreign Application Priority Data
Jul. 31, 2014 (JP) .................................. 2014-156526

(51) Int. Cl.
*B65D 83/10* (2006.01)
*A61B 50/36* (2016.01)
(Continued)

(52) U.S. Cl.
CPC ......... *A61B 50/362* (2016.02); *A61M 5/3205* (2013.01); *A61B 2050/005* (2016.02)

(58) Field of Classification Search
CPC ............ A61B 50/362; A61B 2050/005; A61B 19/0288; A61M 5/3205; A61M 5/3213
(Continued)

(56) References Cited

U.S. PATENT DOCUMENTS 4,738,362 A * 4/1988 Burns ................. A61M 5/3205
206/366
4,862,573 A * 9/1989 Kelson ................ A61M 5/3205
206/366
(Continued)

FOREIGN PATENT DOCUMENTS

JP    S64-20860 A    1/1989
JP    H02-1161 U     1/1990
(Continued)

OTHER PUBLICATIONS

Aug. 3, 2017 Office Action issued in Japanese Patent Application No. 2014-156526.
(Continued)

*Primary Examiner* — Luan K Bui
(74) *Attorney, Agent, or Firm* — Oliff PLC

(57) ABSTRACT

A syringe needle disposal container for disposing of a syringe needle having a needle holder detachably screw-fitted to an end of a syringe body and a needle body, which includes a lid that covers an opening of a container body and a moving member mounted on the lid so as to be slide-movable. A first holding part for holding one side of needle holder is provided at a predetermined part of the lid. The moving member is formed with a second holding part for holding the other side of the needle holder. An open end of the first holding part on the lid side is deviated toward the first holding part with respect to a reference center axis line L that passes through the center P of a syringe needle holding part in the holding position state and that is substantially perpendicular to a slide-moving direction of the moving member.

10 Claims, 14 Drawing Sheets

(51) Int. Cl.
*A61M 5/32* (2006.01)
*A61B 50/00* (2016.01)

(58) Field of Classification Search
USPC ............... 206/363–366; 604/110, 192
See application file for complete search history.

(56) References Cited

U.S. PATENT DOCUMENTS

| | | | | |
|---|---|---|---|---|
| 4,995,871 A * | 2/1991 | Sasaki | ............... | A61M 5/3205 |
| | | | | 206/366 |
| 5,300,028 A * | 4/1994 | Welcheck | ............ | A61M 5/3205 |
| | | | | 206/366 |
| 5,323,900 A * | 6/1994 | Atkins | ............... | A61M 5/3216 |
| | | | | 206/365 |
| 5,356,385 A * | 10/1994 | Latini | ............... | A61M 5/3213 |
| | | | | 206/366 |
| 5,947,950 A * | 9/1999 | Shillington | ......... | A61M 5/3205 |
| | | | | 206/366 |
| 6,247,592 B1 * | 6/2001 | Racicot | ............... | A61M 5/3205 |
| | | | | 206/366 |
| 6,253,916 B1 * | 7/2001 | Bickel | ................ | A61M 5/3205 |
| | | | | 206/366 |
| 8,875,882 B1 * | 11/2014 | Salloum | ............. | A61M 5/3205 |
| | | | | 206/366 |

FOREIGN PATENT DOCUMENTS

| | | |
|---|---|---|
| JP | H10-43256 A | 2/1998 |
| JP | 5444332 B2 | 3/2014 |
| WO | 2010/122683 A1 | 10/2010 |

OTHER PUBLICATIONS

Oct. 13, 2015 Written Opinion issued in International Patent Application No. PCT/JP2015/071308.

Oct. 13, 2015 International Search Report issued in International Patent Application No. PCT/JP2015/071308.

* cited by examiner

SYRINGE NEEDLE DISPOSAL CONTAINER

TECHNICAL FIELD

The present invention relates to syringe needle disposal containers for removing used syringe needles from syringe bodies and disposing of the syringe needles.

BACKGROUND

Syringes used at hospitals or the like include screw-type syringes with a needle holder of a syringe needle freely-detachably screw-fitted to the end of a syringe body. When disposing of this type of syringe after use, the syringe is segregated into the syringe body and the syringe needle in order to prevent infection. At this time, if an operator removes the syringe needle from the syringe body with his/her hand directly grabbing the syringe needle, there is a danger that his/her finger or the like accidentally gets hurt by the syringe needle.

Thus, syringe needle disposal containers capable of safely removing the used syringe needle from the syringe body and disposing of the same have been conventionally used (see Patent Document 1, for example). These syringe needle disposal containers include a container body for containing medical waste and a lid for covering an opening of the container body, and a moving member is freely-movably supported by a mounting part of the lid through a slide mechanism. The mounting part is provided at one end with a first holding part for holding one side of the needle holder of the syringe needle, and the moving member is provided with a second holding part for holding the other side of the needle holder of the syringe needle.

When disposing of the syringe needle into the syringe needle disposal container, first the moving member is moved to a holding position toward the first holding part on the lid side in a predetermined direction, making the first holding part on the lid side and the second holding part on the moving member side form a syringe needle holding part. Then, the needle holder of the syringe needle is inserted into the syringe needle holding part, and in this condition the syringe body is rotated in a detaching direction to remove the needle holder from the syringe body. Thereafter, the moving member is moved to a retract position. As a result, the second holding part of the moving member separates from the needle holder of the syringe needle, and the needle holder (i.e., the syringe needle) held by the first holding part of the lid drops by its own weight through a dropping opening of the lid and is contained into the container body.

RELATED ART

Patent Documents

Patent Document 1: Japanese Patent No. 5444332

SUMMARY

Problems to be Solved by the Invention

The above-described syringe needle disposal container, however, has the following problems. When the moving member is held in the holding position, the first holding part on the lid side and the second holding part on the moving member side form the syringe needle holding part. In the conventional syringe needle disposal container, the open end of the first holding part on the lid side, i.e., a division axis line of the needle holding part is an axis line that passes through the center of the syringe needle holding part and matches an axis line extending in a direction perpendicular to a slide direction of the moving member. Further, the syringe needle holding part is formed on entire peripheral surface. Thus, it is likely that the needle holder (i.e., the syringe needle) does not separate from a predetermined holding part and that the needle holder remains at the predetermined holding part when the moving member is moved toward the retract position.

It is an object of the invention to provide a syringe needle disposal container that can easily remove a syringe needle from a syringe body and let the same drop and be contained into a container body.

Means to Solve the Problems

A syringe needle disposal container according to an embodiment is a syringe needle disposal container for disposing of a syringe needle having a needle holder detachably screw-fitted to an end of a syringe body and a needle body held by the needle holder, and is characterized by including:

a container body for accommodating waste; a lid that covers an opening of the container body; and a moving member mounted on a mounting part provided to the lid by a slide mechanism so as to be slide-movable in a predetermined direction, wherein; the mounting part is formed at one end with a first holding part for holding one side of the needle holder of the syringe needle and with a dropping opening in relation to the first holding part; the moving member is formed with a second holding part for holding the other side of the needle holder of the syringe needle;

when the moving member is moved to a holding position in the predetermined direction, the moving member moves toward the first holding part, and the first holding part on the lid side and the second holding part on the moving member side together form a syringe needle holding part for holding the syringe needle; when the moving member is moved in a direction away from the first holding part, the syringe needle holding part is released, enabling the syringe needle to drop through the dropping opening of the mounting part; and an open end of the first holding part on the lid side is deviated toward the first holding part with respect to a reference center axis line that passes through the center of the syringe needle holding part in the holding position and that is substantially perpendicular to a slide-moving direction of the moving member.

Also, the syringe needle disposal container according to an embodiment is characterized by that a deviation amount D of the open end of the first holding part on the lid side from the reference center axis line is (0.1-0.4)d, i.e., (0.1 d(0.1 d≤D≤0.4 d), wherein d is an outer diameter of the needle holder of the syringe needle.

Also, the syringe needle disposal container according to an embodiment is characterized by that an inner peripheral surface of the second holding part on the moving member side has a holding area that engages the syringe needle and a non-holding area that does not engage the syringe needle.

Also, the syringe needle disposal container according to an embodiment is characterized by that the non-holding area is formed at an open end part that protrudes toward the first holding part beyond the reference center axis line in the second holding part on the moving member.

Also, the syringe needle disposal container according to an embodiment is characterized by that the holding area is engaging protrusions that engage the syringe needle, and the engaging protrusions have a height for engaging vertical ribs formed on an outer peripheral surface of the syringe needle and are formed such that a force in a slide direction does not act on the vertical ribs on the outer peripheral surface of the syringe needle when the moving member slides.

Also, a syringe needle disposal container according to an embodiment is a syringe needle disposal container for disposing of a syringe needle having a needle holder detachably screw-fitted to an end of syringe body and a needle body held by the needle holder and is characterized by including:

a container body for accommodating waste; and a lid that covers an opening of the container body, wherein;

the lid has a first holding part that holds one side of the needle holder of the syringe needle and a second holding part that is freely slide-movable in a direction away from the first holding part, the second holding part holding the other side of the needle holder of the syringe needle and forming a needle dropping opening between the first holding part when moved in the direction away from the first holding part;

when the second holding part is moved to a holding position in the predetermined direction, then the second holding part moves in a direction toward the first holding part, and the first holding part and the second holding part together form a syringe needle holding part for holding the syringe needle; when the second holding part is moved in the direction away from the first holding part, then the syringe needle holding part is released, enabling the syringe needle to drop through the dropping opening;

the second holding part and the first holding part have a holding area for engaging the syringe needle; and the second holding part of the moving member and/or the first holding part on the lid side have a non-holding area that does not engage the syringe needle.

Also, the syringe needle disposal container according to an embodiment is characterized by that the holding area is engaging protrusions that engage the syringe needle, and that the engaging protrusions have a height for engaging vertical ribs formed on an outer peripheral surface of the syringe needle and are formed such that a force in a slide direction does not act on the vertical ribs on the outer peripheral surface of the syringe needle when the moving member slides.

Further, A syringe needle disposal container according to an embodiment is a syringe needle disposal container for disposing of a syringe needle having a needle holder detachably screw-fitted to an end of syringe body and a needle body held by the needle holder, and is characterized by including:

a container body for accommodating waste; and a lid that covers an opening of the container body, wherein:

the lid has a first holding part that holds one side of the needle holder of the syringe needle and a second holding part that is freely slide-movable in a direction away from the first holding part, the second holding part holding the other side of the needle holder of the syringe needle and forming a needle dropping opening between the first holding part when moved in the direction away from the first holding part;

when the second holding part is moved to a holding position in the predetermined direction, then the second holding part moves in a direction toward the first holding part, and the first holding part and the second holding part together form a syringe needle holding part for holding the syringe needle; when the second holding part is moved in the direction away from the first holding part, then the syringe needle holding part is released, enabling the syringe needle to drop through the dropping opening; a an open end of the first holding part is located deviated toward the first holding part with respect to a reference center axis line that passes through the center of the syringe needle holding part in a holding-position state and that is substantially perpendicular to a slide-move direction of the second holding part.

Effects of the Invention

According to the invention, it is possible to provide a syringe needle disposal container capable of removing a syringe needle from a syringe body and letting the same drop and be contained into a container body.

DETAILED DESCRIPTION

Figure 1:
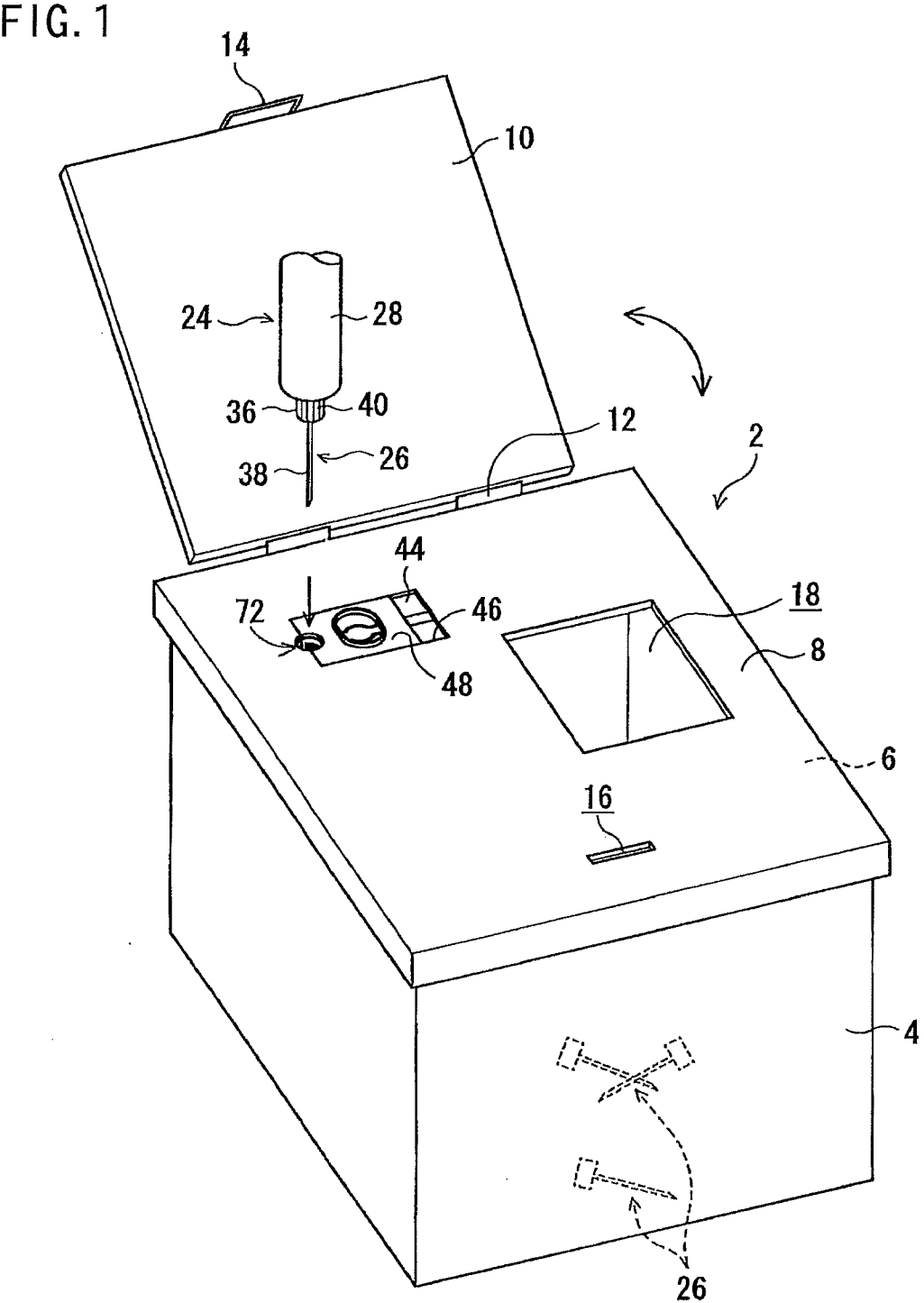
FIG. 1 A perspective showing an embodiment of a syringe needle disposal container according to the present invention FIG. 2 An expanded perspective view of a mounting part and a moving member to be mounted on the mounting part of the syringe needle disposal container of FIG. 1
Figure 2:
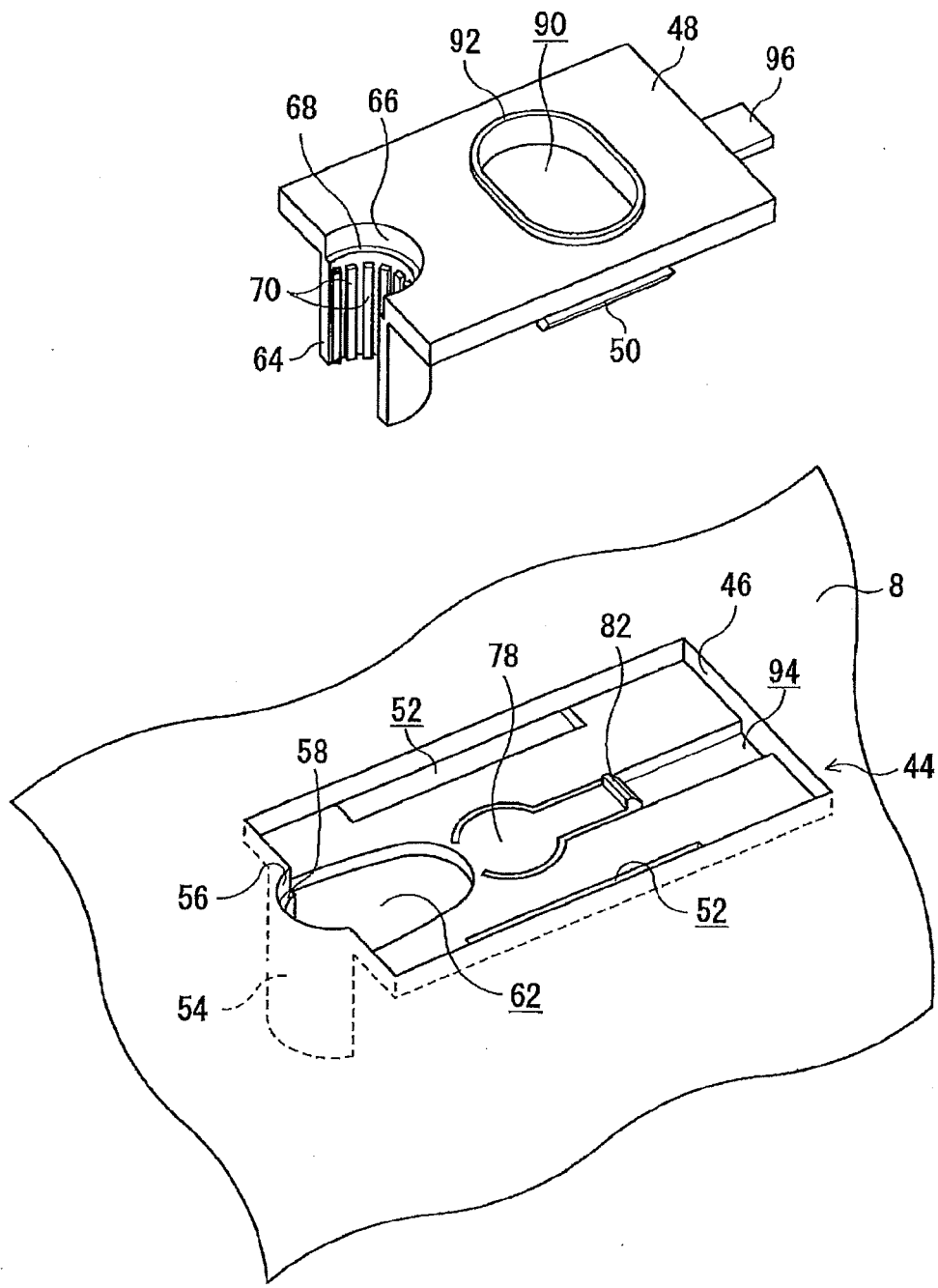
Figure 3:
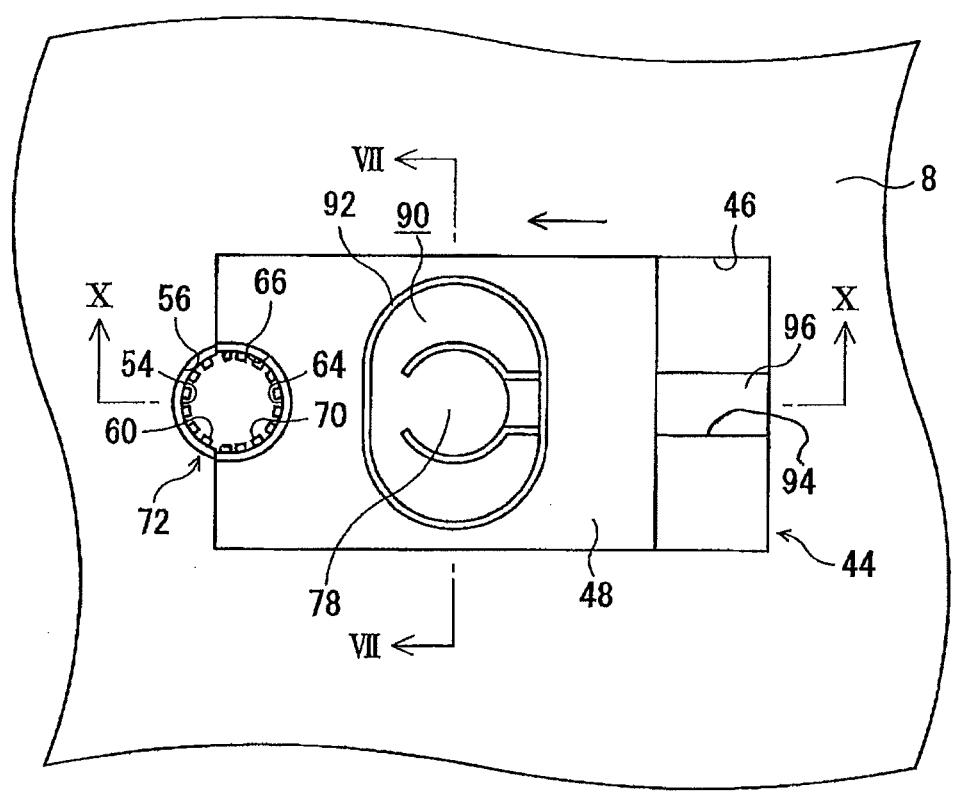
FIG. 3 A view of the moving member positioned at a holding position as viewed from the top FIG. 4 A view of the moving member positioned at a retract position as viewed from the top FIG. 5 A view of the moving member positioned at the holding position as viewed from below FIG. 6 A view of the moving member positioned at the retract position as viewed from below FIG. 7 A cross-sectional view taken along a line VII-VII of FIG. 3
Figure 4:
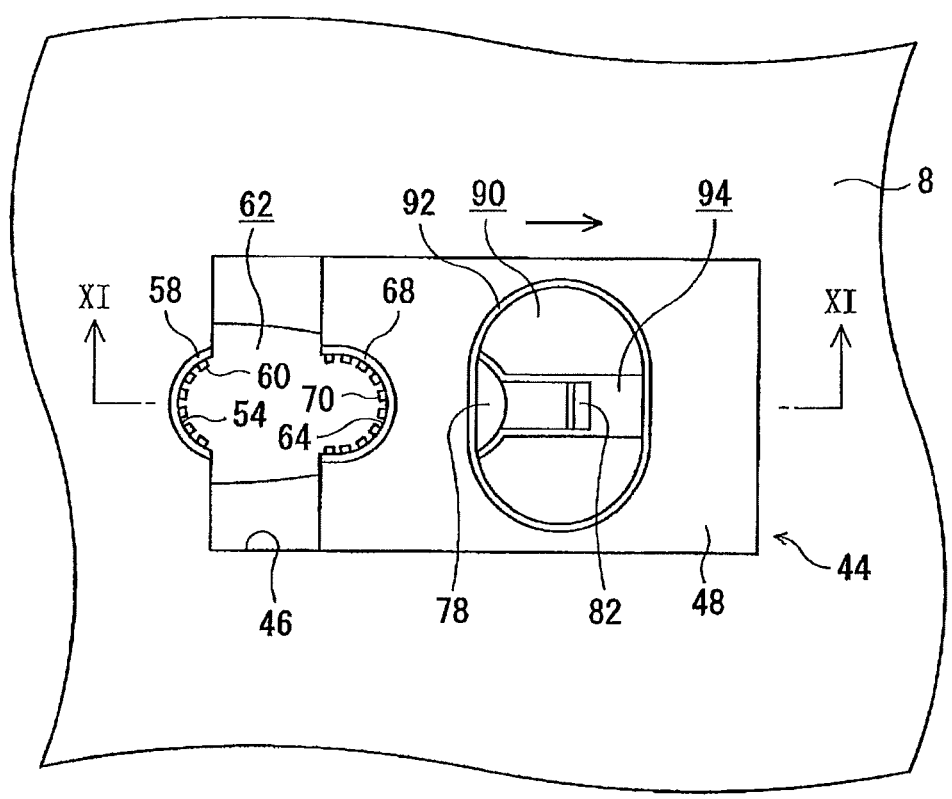
Figure 5:
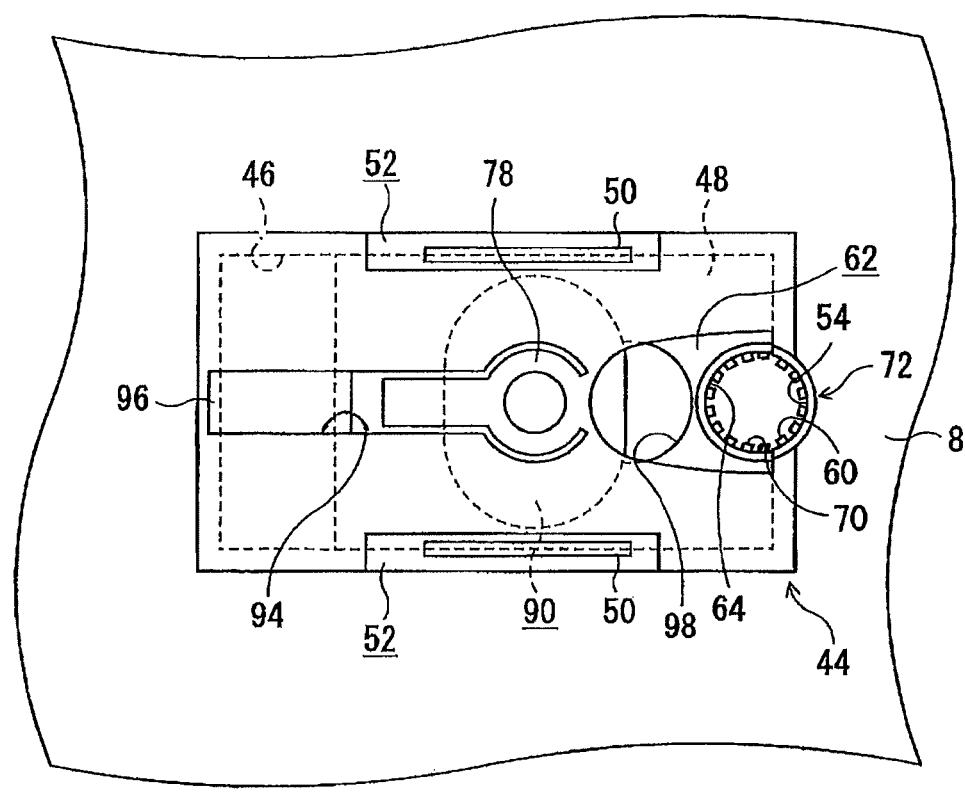
Figure 6:
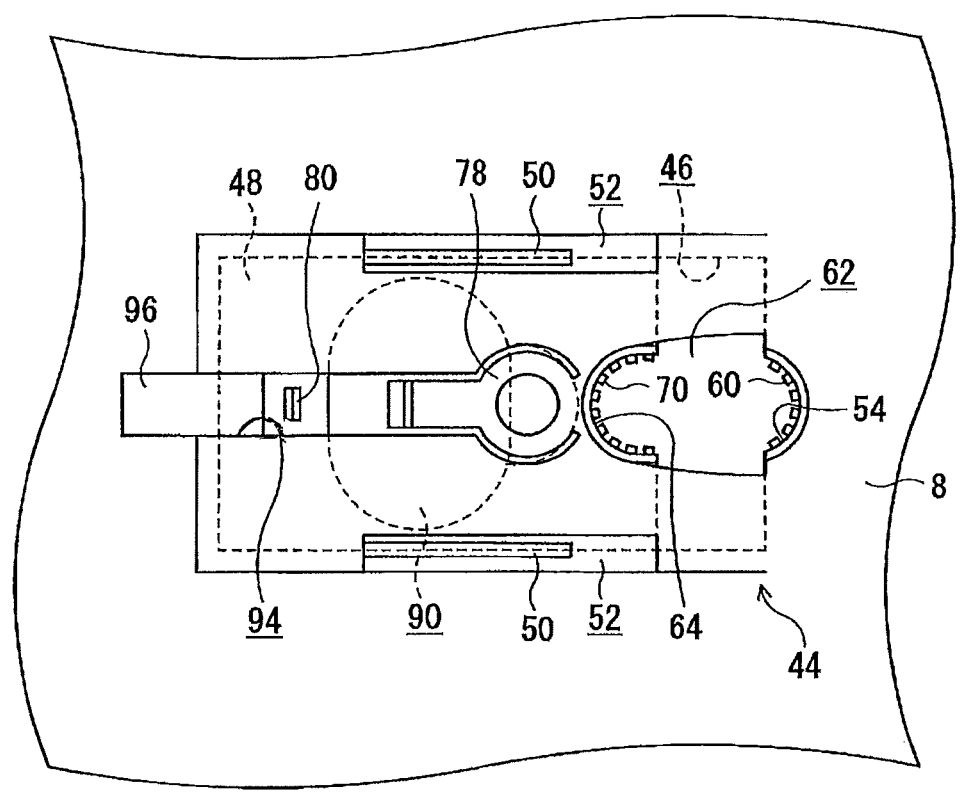
Figure 7:
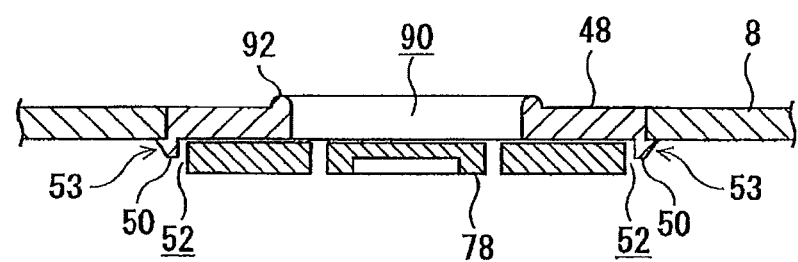

An embodiment of a syringe needle disposal container according to the invention will be described while referring to the accompanying drawings. In FIG. 1, a syringe needle disposal container 2 includes a container body 4 for containing such medical waste as used syringe needles and absorbent cotton. The container body 4 is in an open-top box shape, and an upper opening 6 of the container body 4 is covered with a plate-shaped lid 8. A cover 10 for covering an upper surface of the lid 8 is attached to a rear part of the lid 8 by hinges 12 so as to be freely open and closed. A hook 14 is provided to a front edge of the cover 10, and the lid 8 is formed with a receiving recess 16 in corresponding to the hook 14. The hook 14 is freely detachably received into the receiving recess 16. The lid 8 is formed with a throw-in opening 18 in a rectangle shape. Used absorbent cotton and the like are thrown into the container body 4 through the throw-in opening 18.

The syringe needle disposal container 2 is configured as follows, so that a syringe needle 26 of a screw-type syringe 24 (for example, insulin syringe) can be disposed of With reference to FIGS. 2 to 11 together with FIG. 1, the screw-type syringe 24 includes a syringe body 28, and the syringe needle 26 is screw-fitted to a tip end of the syringe body 28 (see FIGS. 1 and 10). The syringe body 28 is provided, at its end, with a small-diameter protrusion 30, and a needle attaching part 32 is formed at an end of the small-diameter protrusion 30, and a male screw part 34 is formed on a outer peripheral surface of the needle attaching part 32. The syringe needle 26 has a cylindrical needle holder 36 (so called hab) and a needle body 38 supported by the needle holder 36. The needle body 38 is supported by penetrating through an end wall (not shown) of the needle holder 36. The needle holder 36 has an inner peripheral surface forming a female screw part (not shown) corresponding to the male screw part 34 on the syringe body 28 side. With this configuration, screw-fitting the female screw part of the syringe needle 26 to the male screw part 34 of the syringe body 28 attaches the syringe needle 26 to the syringe body 28, forming the syringe 24. Rotating the syringe needle 26 in a removing direction in this state makes it possible to remove the syringe needle 26 from the syringe body 28.

Figure 10:
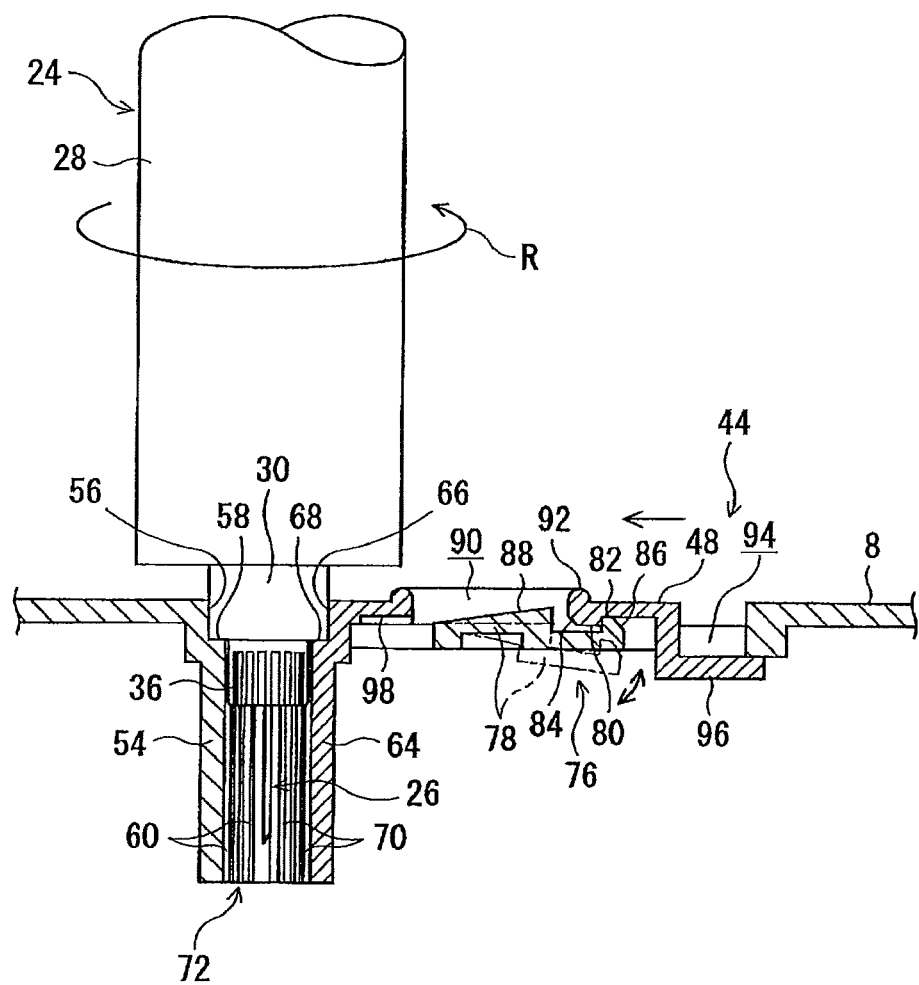

In this embodiment, an outer peripheral surface of the needle holder 36 of the syringe needle 26 is formed with a plurality of (in this embodiment, 16 as shown in FIG. 10) engaging recesses 40 at substantially even intervals in a peripheral direction. The plurality of engaging recesses 40 extends straight in an axis direction of the needle holder 36 (up-down direction in FIGS. 10 and 11). Forming the engaging recesses 40 in this manner forms vertical ribs between neighboring engaging recesses 40. The vertical ribs are formed on the outer peripheral surface of the needle holder 36 in the peripheral direction.

The lid 8 on the container body 4 side is provided with a mounting part 44. The mounting part 44 is formed with a mounting recess 46 in a rectangular shape (see FIG. 2). The mounting recess 46 is formed in the upper surface of the lid 8. The mounting recess 46 is mounted with a plate-shaped moving member 48 so as to be slide-movable along the mounting recess 46. The moving member 48 is provided at both sides with a pair of mounting claws 50 extending in the slide-moving direction of the moving member 48 (right-left direction in FIGS. 3 to 6, 10, and 11, a direction perpendicular to the sheet surface of FIG. 7). The mounting recess 46 is formed at both sides with a pair of mounting openings 52 corresponding to the pair of mounting claws 50. The mounting openings 52 extend in the slide-moving direction. The pair of mounting claws 50 on the moving member 48 side is engaged with edges of the mounting openings 52 through the pair of mounting openings 52 so as to be slide-movable (see FIG. 7). The pair of mounting claws 50 and the pair of mounting openings 52 configure a slide mechanism 53 (see FIG. 7). Through the slide mechanism 53, the moving member 48 is slide-moved between a holding position (a position shown in FIGS. 3, 5, 8, and 10 for holding the syringe needle 26 as described later) and a retract position (a position shown in FIGS. 4, 6, and 11 where holding of the syringe needle 26 is released) retracted from the holding position.

In this embodiment, a substantially-semi-cylindrical first holding part 54 is provided at an end of the mounting part 44 of the lid 8, more specifically, at an end of the mounting recess 46. The first holding part 54 extends downward toward inside of the container body 4. A first holding recess 56 is formed at an upper end of an inner peripheral surface (i.e., a concave inner surface in a substantially semi-arc shape) of the first holding part 54. The first holding recess 56 has a shape corresponding to an outer peripheral shape of the tip end of the small-diameter protrusion 30 of the syringe body 28. When the syringe needle 26 is inserted as described later, an end surface of the small-diameter protrusion 30 of the syringe body 28 abuts a bottom surface 58 of the first holding recess 56 (see FIG. 10).

Most part of the inner peripheral surface of the first holding part 54 is formed with a plurality of engaging protrusions 60 at intervals in the peripheral direction. The plurality of engaging protrusions 60 has a shape corresponding to the shape of the plurality of engaging recesses 40 of the needle holder 36 of the syringe needle 26 (see FIGS. 8, 10, and 11), protrudes inward in the radial direction of the first holding part 54, and extends downward from an upper part to a lower end of the first holding part 54. An area formed with the plurality of engaging protrusions 60 functions as a holding area. Also, the mounting recess 46 is formed on one side (on the first holding part 54 side in this embodiment) with a dropping opening 62. The dropping opening 62 extends in a parabolic shape from the one end to near the center of the mounting recess 46.

Also, the moving member 48 is formed at an end (i.e., an end on the first holding part 54 side) with a substantially semi-cylindrical second holding part 64. The second holding part 64 extends downward toward the inside of the container body 4 through the dropping opening 62. A second holding recess 66 is formed at an upper part of an inner peripheral surface (i.e., a concave inner surface in a substantially semi-arc shape) of the second holding part 64. The second holding recess 66 has a shape corresponding to the shape of the outer peripheral surface of the small-diameter protrusion 30 of the syringe body 28. When the syringe needle 26 is inserted as described later, the end surface of the small-diameter protrusion 30 of the syringe body 28 abuts a bottom surface 68 of the second holding recess 66 (see FIG. 10).

Most part of the inner peripheral surface of the second holding part 64 is formed with a plurality of engaging protrusions 70 at intervals in the peripheral direction. The plurality of engaging protrusions 70 has a shape corresponding to the shape of the plurality of engaging recesses 40 of the needle holder 36 of the syringe needle 26 (see FIGS. 8, 10, and 11), protrudes inward in the radial direction of the second holding part 64, and extends downward from an upper part to a lower end of the second holding part 64. An area formed with the plurality of engaging protrusions 70 functions as a holding area. An area between the plurality of engaging protrusions 60 of the first holding part 54 and the plurality of engaging protrusions 70 of the second holding part 64 is a non-holding area with no engaging protrusions.

In the syringe needle disposal container 2, when the moving member 48 is positioned at the holding position, the end of the moving member 48 contacts or comes close to the end of the mounting recess 46, and the first holding part 54 on the lid 8 side and the second holding part 64 on the moving member 48 side together form a cylindrical syringe needle holding part 72, and the plurality of engaging protrusions 60 and 70 forms engaging protrusions positioned on the inner peripheral surface of the syringe needle holding part 72 at intervals (see FIGS. 3, 5, 8, and 10). Also, the first holding recess 56 of the first holding part 54 and the second holding recess 66 of the second holding part 64 together form a holding recess that detachably receives the tip end of the small-diameter protrusion 30 of the syringe body 28.

Also, when the moving member 48 is positioned at the retract position, the other end of the moving member 48 contacts or comes close to the other end of the mounting recess 46, and the second holding part 64 separates from the first holding part 54, opening the syringe needle holding part 72 (see FIGS. 4, 6, 9, and 11). The first and the second holding parts 54 and 64 will be described later in detail.

In this embodiment, a lock mechanism 76 for locking the moving member 48 at the holding position is provided. The lock mechanism 76 includes a tilting member 78 provided at a center of the mounting recess 46 below the moving member 48 so as to be freely tiltable and a locking protrusion 80 provided to an under surface of the moving member 48. The tilting member 78 is provided at a tip end with a locking claw 82 slightly protruding upward. The locking claw 82 is formed at a tip end with a first taper part 86. Also, the locking protrusion 80 is formed at a tip end with a second taper part 84 corresponding to the first taper part 86 of the locking claw 82.

Figure 11:
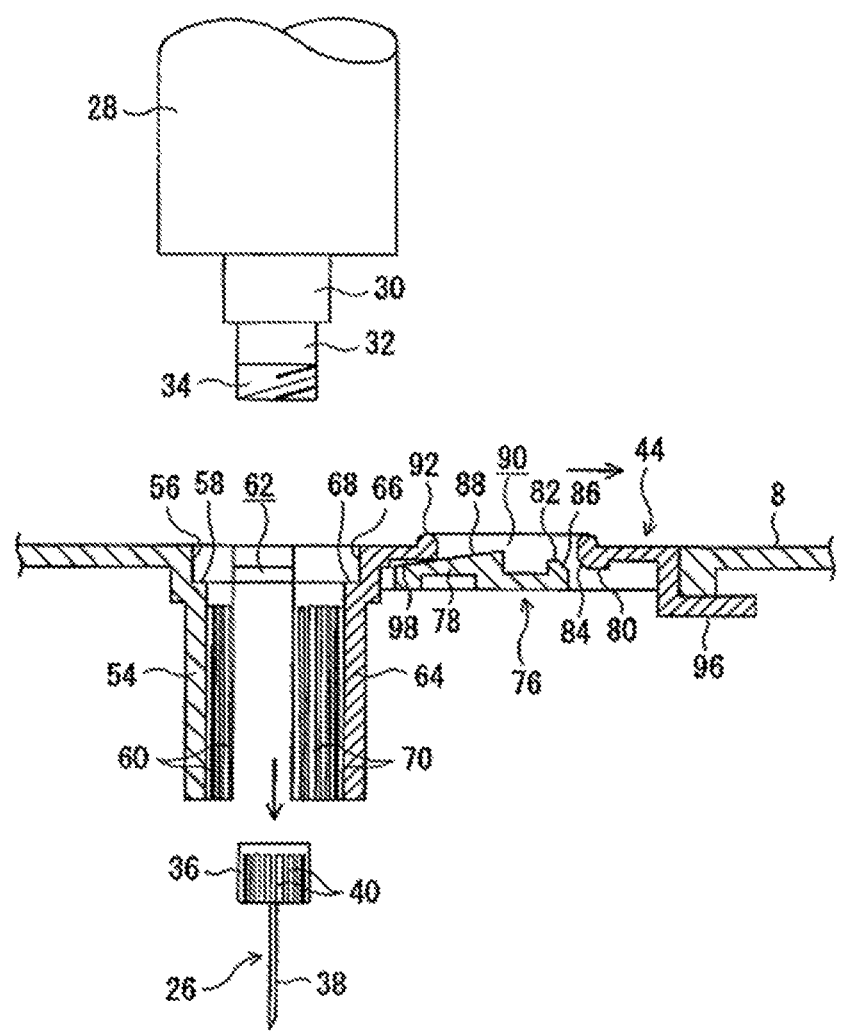
FIG. 11 A cross-sectional view taken along a line XI-XI of FIG. 4

Also, a part of the upper surface of the tilting member 78 forms a slope surface 88 that slopes upward from its base side toward a tip-end side (see FIGS. 10 and 11). Also, the moving member 48 is formed with an operation opening 90 in an oval shape. The upper surface (the slope surface 88) of the tilting member 78 is exposed outside through the operation opening 90. The operation opening 90 is formed at its edge with a ring-shaped operation protrusion 92 slightly protruding upward. With the operation protrusion 92, pressing operation on the slope surface 88 of the tilting member 78 through operation opening 90 is made easier.

The tilting member 78 is capable of freely tilting in the up-down direction between a lock position (indicated with a solid line in FIG. 10) where the locking claw 82 engages the locking protrusion 80 and an unlock position (indicated with a single-dot chain line in FIG. 10) where the locking claw 82 is detached from the locking protrusion 80. The tilting member 78 is resiliently deformable between the lock position and the unlock position, and is normally held at the lock position.

In this embodiment, the mounting recess 46 is formed with a moving opening 94. The moving opening 94 extends along a moving path of the locking protrusion 80. The moving member 48 is provided at the other end (an end opposite from the second holding part 64) with a blinder part 96. The blinder part 96 extends downward in a shape of letter "L". When the moving member 48 is positioned at the holding position, the blinder part 96 covers a part of the moving opening 94 of the mounting recess 46 from below. Also, the lower surface of the moving member 48 is formed with a recessed part 98 between the operation opening 90 an the second holding part 64. The recessed part 98 prevents the moving member 48 moved to the retract position from interfering the upper surface of the tilting member 78 when the moving member 48 is positioned at the retract position (see FIG. 11).

Figure 8:
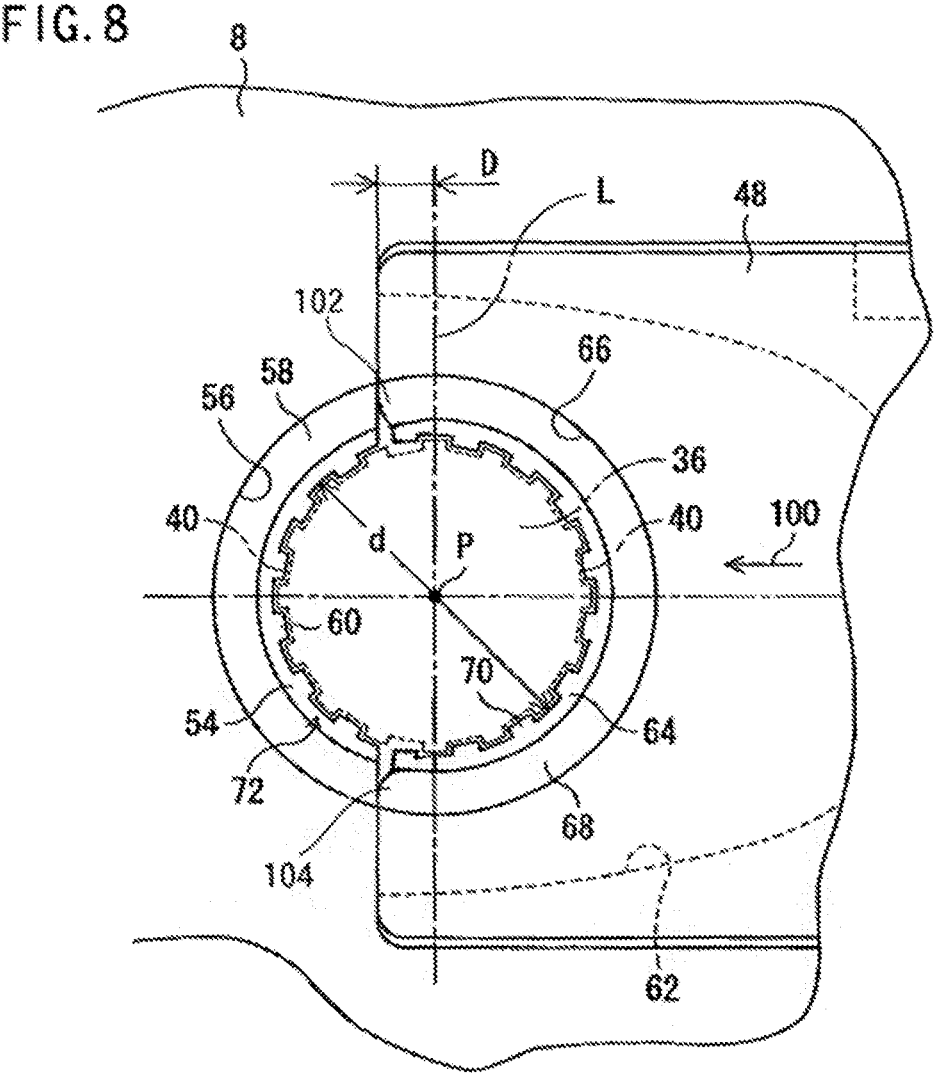
FIG. 8 An enlarged partial plan view showing a syringe needle holding part with the moving member positioned at the holding position and neighboring parts thereof FIG. 9 An enlarged partial plan view showing the syringe needle holding part with the moving member positioned at the retract position and neighboring parts thereof FIG. 10 A cross-sectional view taken along a line X-X of FIG. 3
Figure 9:
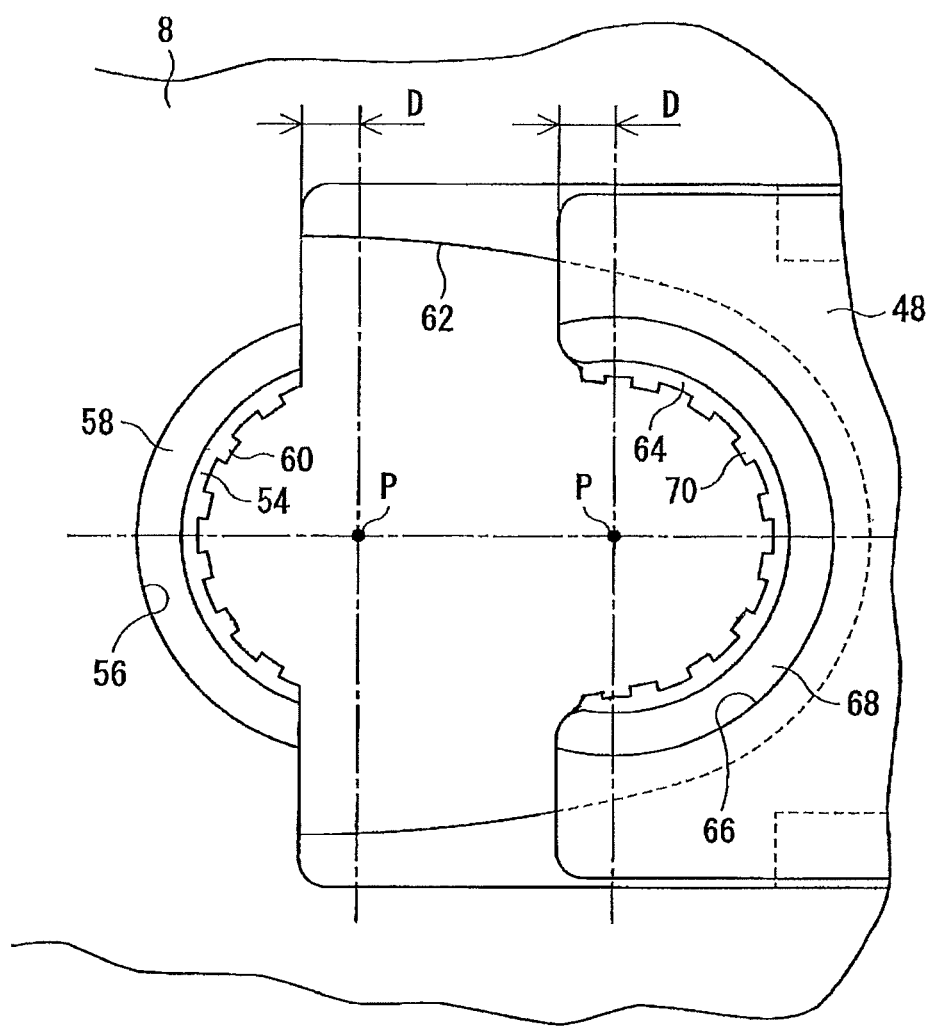

Next, the first holding part 54 on the lid 8 side and the second holding part 64 on the moving member 48 side will be described with reference mainly to FIGS. 8 and 9. In this embodiment, the open end of the first holding part 54 is located deviated toward the first holding part 54 side on the lid 8 side from a reference center axis line L that passes through a center P of the syringe needle holding part 72 formed when the moving member 48 is at the holding position (see FIG. 8) and that is substantially perpendicular to the slide-moving direction indicated by an arrow 100. A deviation amount D (see FIG. 8) of the open end from the reference center axis line L is preferably (0.1~0.4)d, i.e., (0.1 d≤D≤0.4 d), and more preferably (0.15~0.3)d, wherein d is an outer diameter of the needle holder 36 of the syringe needle 26. By deviating the open end of the first holding part 54 from the reference center axis line L toward the first holding part 54 side, more than half of the syringe needle 26 held by the first holding part 54 on the lid 8 side is exposed from the first holding part 54 when the moving member 48 is moved toward the retract position.

Generally, the syringe needle 26 is formed symmetrical about an axis line in an arbitrary radial direction passing through the center, and a position of its center of gravity is at the center P of the syringe needle holding part 72 when it is held by the syringe needle holding part 72. Thus, as will be understood from FIG. 8, when the moving member 48 is moved to the retract position, weight of the syringe needle 26 itself acts as a force for detaching and dropping the same from the first holding part 54 on the lid 8 side, enabling the syringe needle 26 to drop and be contained into the container body 4 with its own weight.

If the deviation amount D of the first holding part 54 is excessively small, then the exposure amount of the syringe needle 26 from the first holding part 54 when the moving member 48 is moved to the retract position becomes smaller, making the detaching-dropping force due to the weight of the syringe needle 26 smaller, causing a danger that the syringe needle 26 does not drop due to its own weight. If the deviation amount D is excessively large, then the engagement between the plurality of engaging protrusions 60 of the first holding part 54 on the lid 8 side and the plurality of engaging recesses 40 of the needle holder 36 of the syringe needle 26 is insufficient, causing a danger that the syringe body 28 is not detached from the syringe needle 26 as described later.

In association with the deviation of the open end of the first holding part 54 from the reference center axis line L toward the first holding part 54 side, it is configured as follow. That is, open end parts 102, 104 of the second holding part 64 on the lid 8 side extend toward the first holding part 54 side beyond the reference center axis line L, and inner surfaces thereof extend slightly outward in the radial direction toward the first holding part 54 side. The inner surfaces of the open end parts 102, 104 are not formed with engaging protrusions for engaging the plurality of engaging recesses 40 of the needle holder 36 on the syringe needle 26 side. The inner surfaces of the open end parts 102, 104 function as non-holding areas. With the open end parts 102, 104 of the second holding part 64 formed to expand in the radial direction and with the inner surfaces of the open end parts 102, 104 formed flat (in other words, formed as the non-holding areas with no engaging protrusions), the open end parts 102, 104 do not act on the syringe needle 26 of the needle holder 36 held by the first holding part 54, making it possible to smoothly move the moving member 48 to the holding position and the retract position. Note that although the inner surfaces of the open end parts 102, 104 of the second holding part 64 are formed to expand outward in the radial direction toward the open end, the inner surfaces may be instead formed straight in a tangential direction toward the open end or straight toward the open end with recessed parts (see FIGS. 12 and 13 to be described later).

Next, a method for disposing of the syringe needle 26 of the screw-type syringe 24 using the above-described syringe needle disposal container 2 will be described. First, the moving member 48 is positioned at the holding position. As a result, as shown in FIG. 10, the locking claw 82 of the tilting member 78 engages the locking protrusion 80 on the lid 8 side, locking the lock mechanism 76. The moving member 48 is locked at the holding position, and the first holding part 54 on the lid 8 side and the second holding part 64 on the moving member 48 side form the syringe needle holding part 72.

Next, in this state, the needle holder 36 of the used syringe needle 26 is inserted into the syringe needle holding part 72 (see FIG. 10). As a result, the end of the small-diameter protrusion 30 of the syringe body 28 abuts the holding recess of the syringe needle holding part 72 (the first holding recess 56 of the first holding part 54 and the second holding recess 66 of the second holding part 64), and the syringe needle 26 is held by the syringe needle holding part 72. In this holding state, the plurality of engaging protrusions 60 and 70 of the first and second holding parts 54 and 64 are held engaged with the plurality of engaging recesses 40 in the outer peripheral surface of the needle holder 36.

Next, with the syringe needle 26 inserted in the syringe needle holding part 72, the syringe body 28 is moved in the detaching direction indicated with an arrow R in FIG. 10 relative to the syringe needle 26. As a result, the screw fit between the female screw part (not shown) of the needle holder 36 and the male screw part 34 of the needle attaching part 32 of the syringe body 28 is released, and the syringe body 28 is removed from the needle holder 36 of the syringe needle 26. At this time, because the moving member 48 is locked at the holding position by the lock mechanism 76, the moving member 48 does not slide-move to the retract position when the syringe body 28 is rotated relative to the syringe needle 26.

Then, a user inserts his/her finger into the operation opening 90 and presses down the upper surface of the tilting member 78, tilting the tilting member 78 downward to release the engagement between the locking claw 82 and the locking protrusion 80 on the lid 8 side (i.e., unlock the lock mechanism 76). In this unlocked condition, the user hooks the finger to the operation protrusion 92 or the like and slide-moves the moving member 48 from the holding position to the retract position. As a result, as shown in FIG. 11, the second holding part 64 on the moving member 48 side is separated from the syringe needle 26 (i.e., the needle holder 36) held by the first holding part 54 on the lid 8 side. The syringe needle 26 tilts toward the moving member 48 by its own weight, and the needle holder 36 is detached from the first holding part 54. Thus detached syringe needle 26 drops and is contained into the container body 4 through the dropping opening 62. In this manner, with the weight of the syringe needle 26 itself, a simple operation to move the moving member 48 to the retract position can put the syringe needle 26 detached from the syringe body 28 into the container body 4.

After collecting the syringe needle 26 into the container body 4, the moving member 48 is slide-moved from the retract position to the holding position for the next collection. At this time, the first taper part 86 of the locking claw 82 slide-moves over the second taper part 84 of the locking protrusion 80. This makes the tilting member 78 tilt downward, engaging the locking claw 82 with the locking protrusion 80. In this manner, the lock mechanism 76 is locked, and the moving member 48 is locked at the holding position.

In the above-described embodiment, the plurality of engaging protrusions 70 is provided to the second holding part 64 on the moving member 48 side in the area from the bottom thereof to the reference center axis line L, i.e., in an 180-degree angle area. Because the engaging protrusions 70 protrude inward in the radial direction, if the protruding amount is set large, there may be a danger that the syringe needle 26 (the needle holder 36) held by the moving member 48 is moved to the retract position when the moving member 48 is moved toward the retract position. Thus, in order to solve such problems, it is preferable to adopt a configuration shown in FIGS. 12 and 13. It should be noted that in this modification, parts substantially the same as those of the embodiment shown in FIGS. 1 to 11 are designated by the same reference numerals, and description thereof will be omitted.

Figure 12:
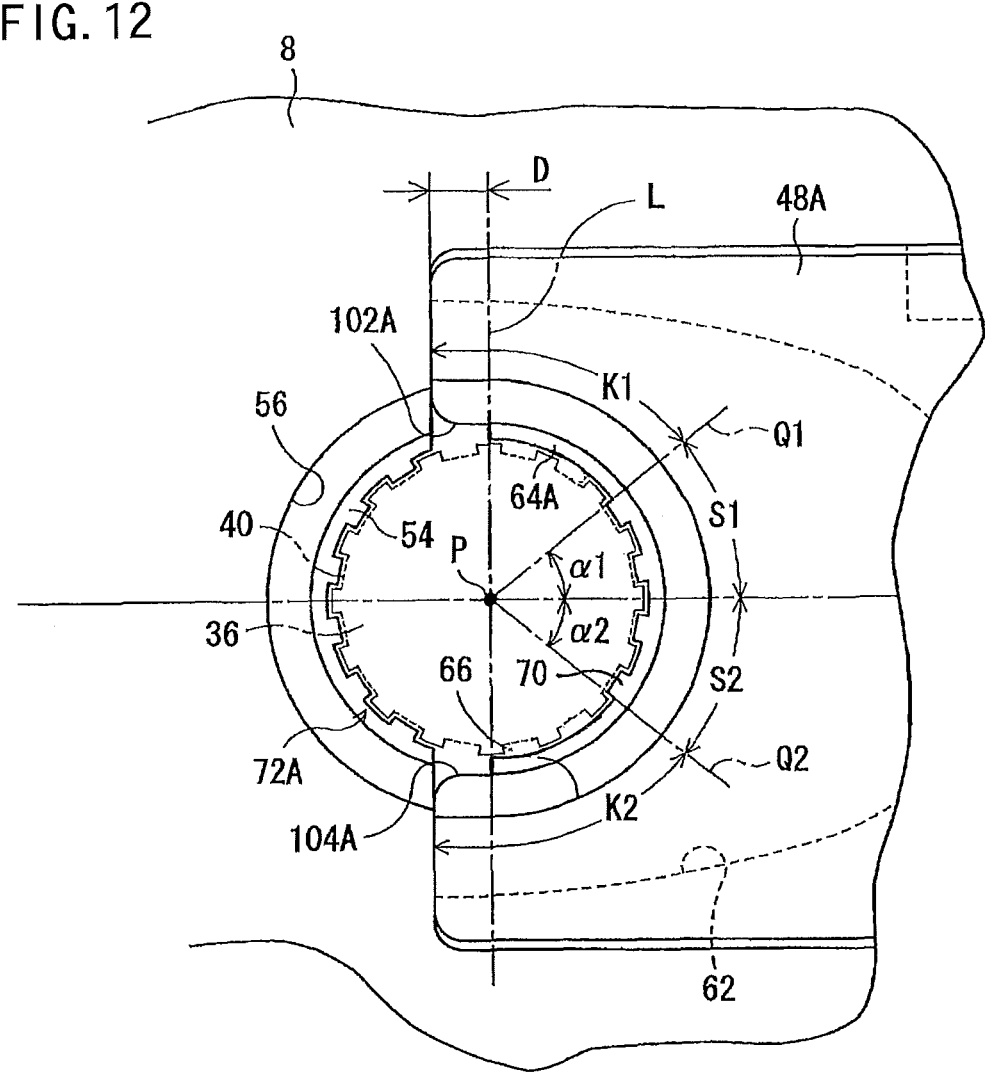
FIG. 12 An enlarged partial plan view of a syringe needle holding part according to a modification with a moving member positioned at the holding position FIG. 13 An enlarged partial plan view of the syringe needle holding part of FIG. 12 with the moving member positioned at the retract position FIG. 14 An enlarged partial plan view of a syringe needle holding part according to another modification with a moving member positioned at the retract position
Figure 13:
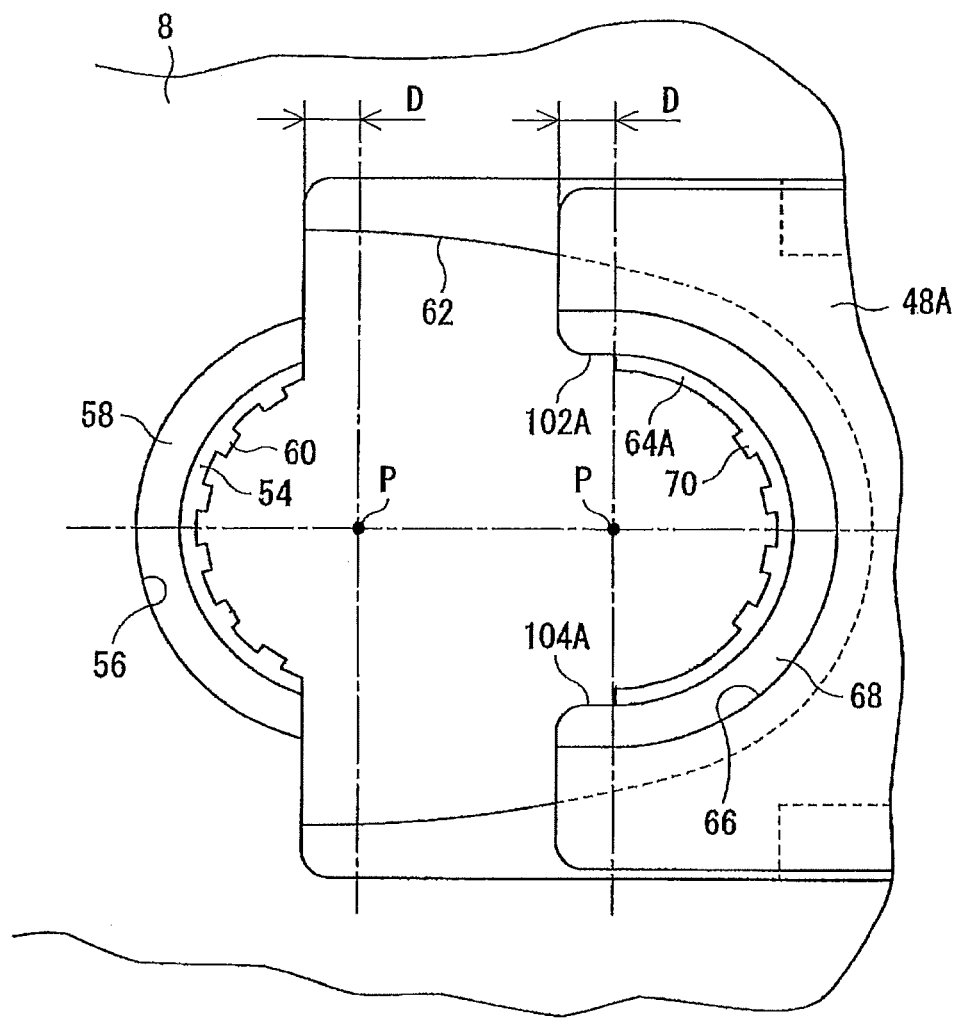

In FIGS. 12 and 13, in this modification, inner surfaces of a first bottom area S1 from a bottom of a second holding part 64A of a moving member 48A to a first predetermined angle $\alpha 1$ on an open end part 102A side on one side and a second bottom area S2 from the bottom to a second predetermined angle $\alpha 2$ on an open end part 104A on the other side are a holding area with the plurality of engaging protrusions 70 formed throughout the bottom areas S1 and S2. The plurality of engaging protrusions 70 engages with the engaging recesses 40 on the other side of the needle holder 36. Also, inner surfaces of a first open area K1 from the first predetermined angle $\alpha 1$ to the open end of the open end part 102A on one side and a second open area K2 from the second predetermined angle $\alpha 2$ to the open end of the open end part 104A on the other side are formed flat, forming a non-holding area. The open areas K1 and K2 are not formed with engaging protrusions for engaging the engaging recesses 40 of the needle holder 36.

The first predetermined angle $\alpha 1$ that is a first border Q1 between the first bottom area S1 and the first open area K1 (non-holding area) is preferably 30 to 70 degrees, and more preferably 35 to 50 degrees. Also, the second predetermined angle $\alpha 2$ that is a second border Q2 between the second bottom area S2 and the second open area K2 (non-holding area) is preferably 30 to 70 degrees, and more specifically between 35 to 50 degrees.

For example, as described above, it may be configured such that two engaging protrusions 70 (holding area) are formed in the first bottom area S1 of a second holding part 64A on the moving member 48A side and that the two engaging protrusions 70 (holding area) are formed in the second bottom area S2, when it is adopted for a syringe needle having the needle holder 36 with the 16 engaging recesses 40 in the outer peripheral surface at even intervals in the radial direction.

If the first and second predetermined angles $\alpha 1$ and $\alpha 2$ defining the first and second bottom areas S1 and S2 are excessively small, then the number of the engaging protrusions 70 for engaging with the engaging recesses 40 of the needle holder 36 becomes small, causing a danger that the engagement between the plurality of engaging recesses 40 of the needle holder 36 and the engaging protrusions 70 of the second holding part 64A becomes insufficient. Also, if the first and second predetermined angles $\alpha 1$ and $\alpha 2$ are excessively large, then it makes harder for the engaging protrusions 70 of the second holding part 64A (especially the engaging protrusions 70 located on the open end part side) to be detached from the engaging recesses 40 of the needle holder 36. Thus, there is a danger that the needle holder 36 moves together with the moving member 48A toward the retract position when the moving member 48A is moved toward the retract position.

The remaining configuration of the modification (such as the configuration of the first holding part 54 on the lid 8 side) may be the same as those described above. In this modification, because the first and second open areas K1 and K2 of the second holding part 64A of the moving member 48A are the non-holding area with no engaging protrusions, the inner surfaces of the first and second open areas K1 and K2 of the second holding part 64A do not act on the needle holder 36 held by the syringe needle holding part 72A. Thus, even when the moving member 48A is moved from the holding position shown in FIG. 12 to the retract position shown in FIG. 13, the needle holder 36 (i.e., the syringe needle) does not move together with the moving member 48A. As a result, it is possible to make the syringe needle (the needle holder 36) remaining on the lid 8 side reliably drop and be contained into the container body with its own weight as described above.

For example, in the above-described embodiment, the first predetermined angle α1 and the second predetermined angle α2 are the same angle. However, it is unnecessary to set both the same. The first predetermined angle α1 may be set larger (or smaller) than the second predetermined angle α2.

While the embodiment and the modification of the syringe needle disposal container according to the invention have been described, the invention is not limited to the embodiment and the modification. Various changes and modifications may be made therein without departing from the spirit of the invention.

For example, in the above-described embodiment, the plurality of engaging recesses 40 are formed in the outer peripheral surface of the needle holder 36 of the syringe needle 26, and the plurality of engaging protrusions 60 and 70 are formed on the inner surfaces of the first holding part 54 on the lid 8 side and the second holding part 64 on the moving member 48 side. On the contrary to this configuration, a plurality of engaging protrusions may be formed on the needle holder 36 side of the syringe needle 26, and a plurality of engaging recesses may be formed on the first and second holding parts 54 and 64 side.

The advantageous effects of the syringe needle disposal container described above are as follows. In this syringe needle disposal container, the moving member is mounted so as to be freely slid-movable between the holding position and the retract position through the slide mechanism. When the moving member is positioned at the holding position, the first holding part on the lid side and the second holding part on the moving member side form the syringe needle holding part for holding the needle holder of the syringe needle. When disposing of the syringe needle of the syringe, the moving member is positioned at the holding position, and the needle holder of the syringe needle is inserted and held in the syringe needle holding part formed of the first and second holding parts. The first holding part on the lid side supports one side of the syringe needle, and the second holding part on the moving member side holds the other side of the syringe needle. If the syringe body is rotated in the detaching direction in this holding state, then the syringe body is removed from the needle holder held by the syringe needle holding part on the container body side. Afterwards, when the moving member is moved to the retract position, the second holding part of the moving member separates from the needle holder of the syringe needle, releasing the holding state. As a result, the syringe needle drops and is contained into the container body through the dropping opening.

Also, the open end of the first holding part on the lid side is positioned deviated toward the first holding part side from the reference center axis line of the syringe needle holding part in the holding position. Therefore, when the moving member is moved to the retract position, more than half of the needle holder of the syringe needle is exposed outside from the first holding part on the lid side, and the position of center of gravity of the syringe needle is outside the first holding part on the lid side. Thus, the weight of the needle holder held by the first holding part on the lid side easily acts as a force for detaching and dropping. Thus, it is possible to drop the syringe needle removed from the syringe body into the container body.

Also, the deviation amount D of the open end of the first holding part on the lid side from the reference center axis line is (0.1~0.4)d, wherein d is the outer diameter of the needle holder of the syringe needle. Thus, when the moving member is moved to the retract position, the center of gravity of the syringe needle held by the first holding part is located at a position distanced by (0.1~0.4)d outward from the open end of the first holding part. Therefore, because of the distance, the weight of the needle holder held by the first holding part acts as a force for detaching and dropping, enabling the syringe needle removed from the syringe body to drop and be contained into the container body.

Also, the outer peripheral surface of the needle holder of the syringe needle is formed with the plurality of engaging recesses (or engaging protrusions) at intervals in the peripheral direction, and the inner surfaces of the first holding part on the lid side and the second holding part on the moving member side are formed with the plurality of engaging protrusions (or engaging recesses) at intervals in the peripheral direction. Thus, the plurality of engaging recesses (or engaging protrusions) on the needle holder side can be engaged with and held by the plurality of engaging protrusions (or engaging recesses) of the first and second holding parts on the container body side.

Also, the outer peripheral surface of the needle holder of the syringe needle is formed with the plurality of engaging recesses, and the inner surfaces of the first holding part on the lid side and the second holding part on the moving member side are formed with the plurality of engaging protrusions. Thus, it can be provided as a disposal container suitable for disposing of this type of syringe needle. Also, the open end part protruding toward the first holding part from the reference center axis line of the second holding part on the moving member extends straight (or widens outward in the radial direction) toward the first holding part on the lid side, and the inner surface of the open end part of the second holding part is not formed with any engaging protrusion. Thus, the open end part of the second holding part does not act on the outer peripheral surface of the needle holder of the syringe needle. Therefore, the syringe needle removed from the syringe body is smoothly dropped into and contained in the container body when the moving member is moved to the retract position.

Also, at the second holding part on the moving member side, the plurality of engaging protrusions are formed in the first bottom area and the second bottom area of the second holding part, and no engaging protrusions are formed in the first open area and the second open area thereof. Thus, when held in the holding position, the plurality of engaging protrusions in the first and the second bottom areas reliably engage with and hold the plurality of engaging recesses of the needle holder of the syringe needle. Also, when moved to the retract position, the plurality of engaging protrusions on the second holding part side does not act on the outer peripheral surface of the needle holder of the syringe needle held by the first holding part on the lid side. Thus, it is possible to prevent the syringe needle from moving to the retract position while held by the second holding part when the moving member is moved to the retract position.

Also, the first predetermined angle as the first border between the first bottom area and the first open area is 30 to 70 degrees, and the second predetermined angle as the second border between the second bottom area and the second open area is 30 to 70 degrees. Thus, when the moving member is moved to the retract position, the plurality of engaging protrusions on the second holding part side does not act on the outer peripheral surface of the needle holder of the syringe needle held by the first holding part on the lid side. Therefore, it is possible to reliably prevent the syringe needle from moving to the retract position while being held by the second holding part when the moving member is moved to the retract position.

Also, the lock mechanism is configured of the tilting member on the lid side and the locking protrusion on the moving member side, and the locking claw is provided at the end of the tilting member. Thus, the engagement between the locking claw of the tilting member and the locking protrusion of the moving member locks the moving member at the holding position. Also, because the upper surface of the tilting member is exposed outside through the operation opening, a finger or the like can be inserted through the operation opening, and the upper surface of the tilting member can be pressed down with the finger or the like to release the lock state. In addition, it is possible to perform, in a single performance, both the operation for tilting to the lock releasing position and the operation for slide-moving the moving member to the retract position with the finger or the like hooked to the operation opening.

Also, the inner surface of the second holding part on the moving member side has the holding area that engages with the syringe needle and the non-holding area that does not engage with the syringe needle. Thus, it is possible to reduce the possibility that the syringe needle remains at the second holding part after the moving member slides to the retract position.

Also, the non-holding area is provided to a part that protrudes toward the first holding part from the reference center axis line of the second holding part on the moving member side. That is, the non-holding area is located on the open side of the second holding part. Thus, the syringe needle is easily removed from the second holding part after the moving member slides to the retract position, and easily drops into and is contained in the container body.

Also, the holding area is the engaging protrusions that engage with the syringe needle, and the engaging protrusions have the height that engages with the vertical ribs formed on the outer peripheral surface of the syringe needle and are formed in the shape such that force in the sliding direction does not at on the vertical ribs on the outer peripheral surface of the syringe needle when the moving member slides. Thus, when the moving member slides, the syringe needle does not slide by being held on the moving member side, and the syringe needle reliably drops into and is contained in the container body.

As an application modification of the invention may be as follows. That is, the second holding part of the moving member and the first holding part on the lid side have the holding area for engaging with the syringe needle, and the second holding part of the moving member and/or the first holding part on the lid side have the non-holding area that does not engage with the syringe needle. The non-holding area is provided on the open end part side of the holding part, and the holding area is the engaging protrusions that engage with the syringe needle. The engaging protrusions have the height that engages with the vertical ribs formed on the outer peripheral surface of the syringe needle, and are formed in the shape such that any force in the slid direction does not act on the vertical ribs on the outer peripheral surface of the syringe needle when the moving member slides. In this case, the holding area of the first holding part on the lid side and the second holding part on the moving member side, no force in the sliding direction acts on the syringe needle when the moving member slides. That is, the holding part is formed incapable of holding the syringe needle when the moving member slide-moves. Thus, as the moving member slide moves, the syringe needle drops and is contained into a disposal container by itself. Note that in this embodiment, the open end of the first holding part on the lid side is not necessarily positioned deviated toward the first holding part side from the reference center axis line that passes through the center of the syringe needle holding part at the holding position and that is substantially perpendicular to the slide-moving direction of the moving member.

Figure 14:
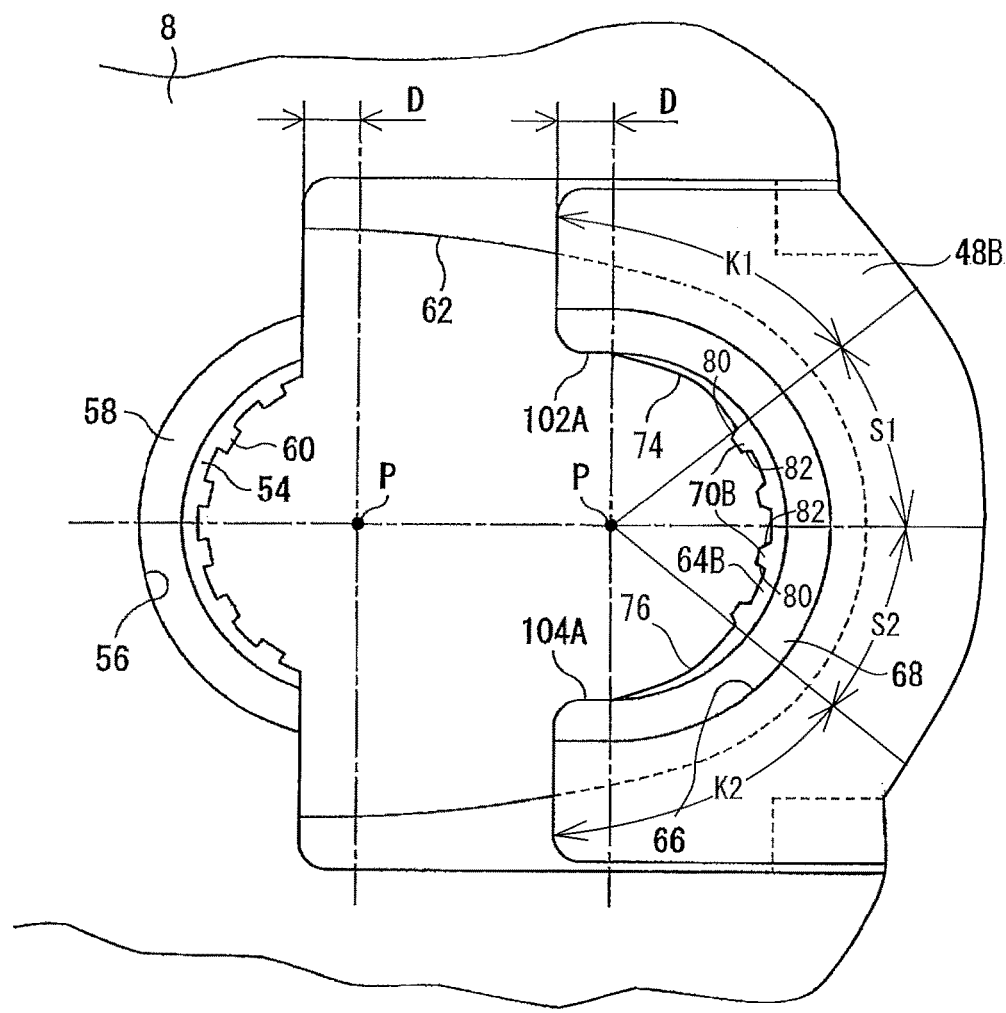

This modification is configured such that force in the slid direction does not act on the vertical ribs of the syringe needle when the moving member moves toward the retract position, as shown in FIG. 14, for example. That is, open-side parts 74, 76 in the non-holding areas K1, K2 of a second holding part 64B are formed with inner diameters increase toward the open side, and thus the open-side parts 74, 76 of the second holding part 64B are formed to slightly widen toward the open end sides more than a semi-circle shape. With this configuration, the inner surface of the second holding part 64B does not act on the vertical ribs of syringe needle 26 when the moving member 48B moves toward the retract position, making it possible to prevent force from the moving member 48B from acting on the vertical ribs.

In addition, each engaging protrusion 70B provided to the second holding part 64B has both side surfaces 80, 82 that slop inward toward the ends (i.e., inward in the radial direction), such that each engaging protrusion 70B has a trapezoidal shape in a horizontal cross-section. With this configuration, the plurality of engaging protrusions 70B of the second holding part 64B does not act on the vertical ribs of the syringe needle 26 when the moving member 48 moves toward the retract position, and it is possible to prevent the force from the moving member 48B through the engaging protrusions 70B from acting on the vertical ribs of the syringe needle 26. Thus, when the moving member 48B is moved toward the retract position, the needle holder 36 of the syringe needle 26 does not taken by the moving member 48B. Note that such sloping of the side surfaces 80, 82 of each engaging protrusion 70B is not necessarily provided to both side surfaces, but may be provided to one side (that is, the side surface 82 opposite to open end parts 102A, 104A to achieve desired effects.

As described above, forming the non-holding area to the first holding part and/or the second holding part prevents the syringe needle from remaining at a predetermined holding part. As a result, it is possible to provide the syringe needle disposal container that can easily make the syringe needle detach from the syringe body and drop and be contained into the container body.

Although the above is the embodiment based on the drawings, the present invention is not limited to the embodiment. For example, in the embodiment, the first holding part is formed at one end of the mounting part, and the second holding part is formed at one end of the moving member. The mounting part may, however, have two moving members capable of freely sliding, and the first holding part and the second holding part may be formed at two holding parts respectively. That is, the syringe needle holding part may be formed by a plurality of moving members.

EXPLANATION OF REFERENCES 2 syringe needle disposal container
4 container body
8 lid
26 syringe needle
28 syringe body
36 needle holder
40 engaging recesses
44 mounting part
48, 48A, 48B moving member
50 mounting claw
52 mounting opening
54 first holding part
60, 70 engaging protrusion
62 dropping opening
64, 64A, 64B second holding part
72 syringe needle holding part
76 lock mechanism

What is claimed is:

1. A syringe needle disposal container for disposing of a syringe needle having a needle holder detachably screw-fitted to an end of a syringe body and a needle body held by the needle holder, comprising:
   a container body for accommodating waste, the container body being formed with an opening;
   a lid that covers the opening of the container body, the lid having a mounting part; and
   a moving member mounted on the mounting part of the lid as to be slide-movable in a first direction and a second direction opposite to the first direction, wherein:
   the mounting part is formed with a first holding part adapted for holding one side of the needle holder of the syringe needle;
   the moving member is formed with a second holding part adapted for holding an other side of the needle holder of the syringe needle;
   when the moving member is moved in the first direction toward the first holding part to the holding position, then the first holding part and the second holding part together form a syringe needle holding part for holding the syringe needle;
   when the moving member is moved in the second direction from the holding position, the syringe needle holding part is released, enabling the syringe needle to fall from the syringe needle holding part; and
   when the moving member is located in the holding position, both of an open end of the first holding part and an open end of the second holding part are deviated in the first direction with respect to a reference center axis line that passes through the center of the syringe needle holding part in the holding position and that is substantially perpendicular to the first and second directions;
   the second holding part has a holding area and a non-holding area, the holding area being formed with engaging protrusions configured to engage the syringe needle, the non-holding area being formed with no engaging protrusions; and
   the non-holding area of the second holding part extends in the first direction beyond the reference center axis line when the moving member is located in the holding position.

2. The syringe needle disposal container according to claim 1, wherein a deviation amount D of the open end of the first holding part from the reference center axis line is (0.1-0.4)d, i.e., (0.1 d≤D≤0.4 d), wherein d is an outer diameter of the needle holder of the syringe needle, and D is a distance between the open end of the first holding part and the reference center axis line.

3. The syringe needle disposal container according to claim 1, wherein the engaging protrusions have a height for engaging vertical ribs formed on an outer peripheral surface of the syringe needle and are formed such that a force in the second direction does not act on the vertical ribs on the outer peripheral surface of the syringe needle when the moving member slides.

4. The syringe needle disposal container according to claim 1, further comprising a lock member that locks the second holding part at the holding position.

5. The syringe needle disposal container according to claim 1, wherein the open end of the second holding part is wider than the open end of the first holding part.

6. A syringe needle disposal container for disposing of a syringe needle having a needle holder detachably screw-fitted to an end of syringe body and a needle body held by the needle holder, comprising:
   a container body for accommodating waste, the container body being formed with an opening; and
   a lid that covers the opening of the container body, wherein:
   the lid has a mounting art and a moving member capable of moving in a first direction and a second direction opposite to the first direction relative to the mounting part;
   the mounting part has a first surface formed with a first holding part;
   the moving member has a second surface confronting the first surface, the second surface being formed with a second holding part,
   when the moving member is moved in the first direction to a holding position, then the second surface comes into direct contact with the first surface, and the first holding part and the second holding part together form a syringe needle holding part for holding the syringe needle;
   the syringe needle holding part has a pair of holding areas each formed with engaging protrusions configured to engage the syringe needle and a non-holding area formed with no engaging protrusions, the non-holding area being located between the pair of engaging areas; and
   when the moving member is moved in the second direction from the holding position, then the second surface separates from the first surface and the syringe needle holding part is released, enabling the syringe needle to fall from the syringe needle holding part.

7. The syringe needle disposal container according to claim 6, wherein: the engaging protrusions have a height for engaging vertical ribs formed on an outer peripheral surface of the syringe needle and are formed such that a force in the second direction does not act on the vertical ribs on the outer peripheral surface of the syringe needle when the moving member slides.

8. A syringe needle disposal container for disposing of a syringe needle having a needle holder detachably screw-fitted to an end of syringe body and a needle body held by the needle holder, comprising:
   a container body for accommodating waste, the container body being formed with an opening; and
   a lid that covers the opening of the container body, wherein:
   the lid has a first holding part configured to hold one side of the needle holder of the syringe needle and a second holding part configured to hold an other side of the needle holder, the second holding part being slide-movable in a first direction toward the first holding part and a second direction opposite to the first direction;

when the second holding part is moved in the first direction to a holding position then the first holding part and the second holding part together form a syringe needle holding part for holding the syringe needle;

when the second holding part is moved in the second direction from the holding position, then the syringe needle holding part is released, enabling the syringe needle to fall from the syringe needle holding part; and when the second holding part is located in the holding position, both of an open end of the first holding part and an open end of the second holding part are deviated in the first direction with respect to a reference center axis line that passes through the center of the syringe needle holding part and that is substantially perpendicular to the first and second directions;

the second holding art has a holding area and a non-holding area, the holding area being formed with engaging protrusions configured to engage the syringe needle, the non-holding area being formed with no engaging protrusions; and when the second holding part is located in the holding position, the non-holding area of the second holding part extends in the first direction beyond the reference center axis line.

9. The syringe needle disposal container according to claim 8, further comprising a lock member that locks the second holding part at the holding position.

10. The syringe needle disposal container according to claim 8, wherein the open end of the second holding part is wider than the open end of the first holding part.

* * * * *